(12) United States Patent
Cusyatiner et al.

(10) Patent No.: US 7,220,572 B2
(45) Date of Patent: May 22, 2007

(54) METHOD FOR PRODUCING L-LEUCINE

(75) Inventors: Mikhail Markovich Cusyatiner, Moscow (RU); Elvira Borisovna Voroshilova, Moscow (RU); Yulia Georgievna Rostova, Moscow (RU); Lirina Valerievna Ivanovskaya, Moscow (RU); Maria Grigorievna Lunts, Moscow (RU); Evgeniy Moiseevich Khourges, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 462 days.

(21) Appl. No.: 10/601,634

(22) Filed: Jun. 24, 2003

(65) Prior Publication Data

US 2004/0091980 A1 May 13, 2004

(30) Foreign Application Priority Data

Jun. 25, 2002 (RU) ............................. 2002116773

(51) Int. Cl.
*C12N 1/20* (2006.01)
*C12P 13/06* (2006.01)
*C12N 15/00* (2006.01)
*C12N 9/10* (2006.01)
*C12P 21/06* (2006.01)
*C12P 13/08* (2006.01)
*C12Q 1/48* (2006.01)
*C07K 14/00* (2006.01)
*C07H 21/04* (2006.01)

(52) U.S. Cl. ............................. 435/252.33; 435/252.3; 435/320.1; 435/69.1; 435/193; 435/15; 435/116; 435/440; 435/115; 530/350; 536/23.1; 536/23.2

(58) Field of Classification Search ............ 435/252.3, 435/252.33, 320.1, 69.1, 193, 15, 116, 440, 435/115; 530/350; 536/23.1, 23.2
See application file for complete search history.

(56) References Cited

U.S. PATENT DOCUMENTS 5,120,654 A 6/1992 Marquardt et al.
5,744,331 A 4/1998 Nakano et al.
5,763,231 A 6/1998 Ono et al.
6,214,591 B1 4/2001 Tomita et al.

FOREIGN PATENT DOCUMENTS

| EP | 0 297 619 | 1/1989 |
| EP | 0 533 216 | 3/1993 |
| EP | 1 067 191 | 1/2001 |
| RU | 2 140 450 | 10/1999 |

OTHER PUBLICATIONS

Seffernick et al., J. Bacteriol. 183(8):2405-2410, 2001.*
Witkowski et al., Biochemistry 38:11643-11650, 1999.*
Branden et al., Introduction to Protein Structure, Garland Publishing Inc., New York, p. 247, 1991.*
Vartak et al., J. Bacteriol. 173(12):3864-3871, 1991.*
J. T. Powell, et al., Journal of Bacteriology, vol. 136, No. 1, XP-008022967, pp. 1-4, "Role of the *Escherichia coli* Aromatic Amino Acid Aminotransferase in Leucine Biosynthesis", Oct. 1978.
D. H. Gelfand, et al., Journal of Bacteriology, vol. 130, No. 1, XP-008022968, pp. 429-440, "*Escherichia coli* Mutants Deficient in the Aspartate and Aromatic Amino Acid Aminotransferases", Apr. 1977.
N. B. Vartak, et al., Journal of Bacteriology, vol. 173, No. 12, XP-008022971, pp. 3864-3871, "A Functional leuABCD Operon is Required for Leucine Synthesis by the Tyrosine-Repressible Transaminase in *Escherichia coli* K-12", Jun. 1991.
M. Kisumi, et al., Journal of Biochem, vol. 80, No. 2, pp. 333-339, "Biosynthesis of Norvaline, Norleucine, and Homoisoleucine in Serratia Marcescens", 1976.

* cited by examiner

*Primary Examiner*—Delia M. Ramirez
(74) *Attorney, Agent, or Firm*—Oblon, Spivak, McClelland, Maier & Neustadt, P.C.

(57) ABSTRACT

There is provided a method for producing L-leucine using bacterium belonging to the genus *Escherichia*, which produces L-valine, L-isoleucine and L-homoleucine in an amount of less than 1% of that of L-leucine produced due to inactivation of ilvE gene coding for branched chain amino acid transaminase and produces increased amount of L-leucine due to increasing the activity of the aromatic amino acid transaminase encoded by tyrB gene.

4 Claims, 1 Drawing Sheet

METHOD FOR PRODUCING L-LEUCINE

BACKGROUND OF THE INVENTION

1. Field of the Invention

The present invention relates to microbiological industry, specifically to a method for producing amino acids. More specifically, the present invention concerns a method for producing L-leucine using bacterium belonging to the genus *Escherichia* wherein the amount of L-valine, L-isoleucine and L-homoleucine produced is less than 1% of that of L-leucine produced.

2. Description of the Related Art

Conventionally L-amino acids have been industrially produced by a method of fermentation utilizing strains of microorganisms obtained from natural sources or mutants of the same especially modified to enhance the L-amino acids productivity.

Various strains belonging to the genus *Escherichia* used for production of L-leucine by fermentation are known. There are strains resistant to L-leucine and its analogs, such as 4-azaleucine or 5,5,5-trifluoroleucine (U.S. Pat. No. 5,744,331), β-2-thienylalanine and β-hydroxyleucine (U.S. Pat. No. 5,763,231), L-valine, 4-azaleucine, 3-hydroxyleucine and L-leucine (Russian patent RU 2140450); strains requiring lipoic acid for growth (U.S. Pat. No. 6,214,591); strains with increased activities of the enzymes involved in L-leucine biosynthesis, such as ilvE gene product (U.S. Pat. No. 5,120,654); strains with the target enzymes desensitized to the feedback inhibition by produced L-leucine, such as isopropylmalate synthase (European patent EP1067191).

The most known L-leucine producing strains simultaneously produce L-valine and in the small extent L-isoleucine. For example, *E. coli* strain AJ11478 (U.S. Pat. No. 5,763,231) produces simultaneously 1.9 g/l of L-leucine and 0.09 g/l of L-valine (amount of L-valine is 4.7% of L-leucine amount). L-valine and L-isoleucine produced simultaneously with L-leucine inconvenience the recovery of L-leucine from cultural liquids. Besides, L-valine and L-isoleucine co-production decreases L-leucine production since both amino acids are originated from a common precursor, 2-ketoisovalerate.

Earlier it was shown, the unnatural amino acids, such as norvaline, homoisoleucine and norleucine, could be formed by L-leucine biosynthetic enzymes in *Serratia marcescens* from α-ketobutyrate, α-keto-β-methylvalerate and α-ketovalerate, respectively (Kisumi M., Sugiura M. and Chibata I., J. Biochem. 1976, 80(2) 333–9).

DISCLOSURE OF THE INVENTION

An object of the present invention is to obtain an L-leucine producing bacterium, which produces L-valine, L-isoleucine and L-homoleucine in an amount of less than 1% of that of L-leucine produced.

This aim was achieved by inactivation of ilvE gene, encoding branched chain amino acid aminotransferase.

The inactivation of the ilvE gene decreases the L-leucine production, as this aminotransferase participates in L-leucine formation from its keto-precursor, 2-keto-methyl-pentanoate. Another aminotransferase, which could participate in L-leucine production, is aromatic amino acid transaminase encoded by the tyrB gene. Therefore, to restore or even increase L-leucine production when the ilvE gene is inactivated, the increasing of activity of the enzyme, encoded by the tyrB gene was performed, for example, by transformation of the bacterium with a multicopy plasmid containing tyrB gene.

Thus the present invention has been completed.

Thus, the present invention provides an L-leucine producing bacterium belonging to the genus *Escherichia*, which produces L-valine, L-isoleucine or L-homoleucine in an amount of less than 1% of that of L-leucine produced. Further, the present invention provides an L-leucine producing bacterium belonging to the genus *Escherichia*, which produces L-valine, L-isoleucine or L-homoleucine in an amount of less than 1% of that of L-leucine produced, and L-leucine production is increased by increasing activity of the enzyme, encoded by the tyrB gene.

The present invention further provides a method for producing L-leucine by fermentation comprising the steps of cultivating the aforementioned bacterium in a culture medium to produce and accumulate the L-leucine in the medium, and collecting the L-leucine from the medium.

So, the present inventions provides:

(1). An L-leucine producing bacterium belonging to the genus *Escherichia*, which produce L-valine, L-isoleucine and L-homoleucine in an amount of less than 1% of that of L-leucine produced.

(2). The bacterium according to (1) wherein the bacterium produces L-valine, L-isoleucine and L-homoleucine in an amount of less than 1% of that of L-leucine produced, due to inactivation of ilvE gene or decreasing activity of the protein coded by ilvE gene.

(3). The bacterium according to (2) wherein the activity of the protein coded by tyrB gene is increased.

(4). The bacterium according to (3) wherein the activity of the protein coded by tyrB gene is increased by transformation of the bacterium with a DNA containing tyrB gene.

(5). The bacterium according to (4) wherein the transformation is performed using a multicopy vector.

(6). A method for producing the L-leucine, which method comprises the steps of:
cultivating the bacterium according to any of (1) to (5) in a medium to produce and accumulate the L-leucine in the medium, and
collecting the L-leucine from the medium.

(7). The method according to (6), wherein the bacterium has been modified to have enhanced expression of a gene of L-leucine biosynthesis.

The present invention is described in details below.

1. Bacterium of the Present Invention

The bacterium of the present invention is a bacterium belonging to the genus *Escherichia*, which produce L-valine, L-isoleucine and L-homoleucine in an amount of less than 1% of that of L-leucine produced.

The term "L-leucine producing bacterium" used herein means a bacterium, which is able to produce and accumulate L-leucine in a culture medium in an amount of larger than a wild type or parental strain of *E. coli*, such as *E. coli* K-12 strain, and preferably means that the microorganism is able to produce and accumulate in a medium an amount of not less than 0.5 g/L, more preferably not less than 1.0 g/L of L-leucine.

The term "a bacterium belonging to the genus *Escherichia*" means that the bacterium is classified as the genus *Escherichia* according to the classification known to a person skilled in the microbiology. As examples of the microorganism belonging to the genus *Escherichia* used in the present invention, *Escherichia coli* (*E. coli*) can be mentioned.

The term "produce L-valine, L-isoleucine and L-homoleucine in an amount of less than 1% of that of L-leucine produced" means that the amount of L-valine, L-isoleucine and L-homoleucine, which is present in the culture medium after completion of cultivation of L-leucine producing bacterium, is significantly less compared to the amount of main product, L-leucine. Amount of L-valine, L-isoleucine and L-homoleucine in the culture medium is significantly less compared to the amount of L-leucine when, for example, the amount of L-valine, L-isoleucine or L-homoleucine each is less than 1%, preferably less than 0.5%, more preferably less than 0.1% of the amount of the L-leucine produced. It preferably means that the amount of L-valine, L-isoleucine and L-homoleucine could be even not detectable by conventional methods, for example, by thin layer chromatography (TLC) or HPLC.

The term "inactivation of ilvE gene" means that the target gene is modified in the way that the modified gene encodes for a mutant enzyme (inactive enzyme) whose activity is not detectable by known methods or the modified gene is unable to express any enzyme. The ilvE gene codes for branched chain amino acid transaminase (309 amino acid residues), which is able to catalyze reactions of amination of α-ketocarboxylic acids and its salts. The branched chain amino acid transaminase, for example, converts α-ketocaproate into L-leucine, α-ketoisovalerate into L-valine, α-keto-β-methylvalerate into L-isoleucine. The ilvE gene (numbers 3950107 to 3951036 in the GenBank accession number NC_000913.1, gi:16131628) is located between ilvM and ilvD genes. Inactivation of the gene can be performed by conventional methods, such as mutagenesis treatment using UV irradiation or nitrosoguanidine (N-methyl-N'-nitro-N-nitrosoguanidine) treatment, site-directed mutagenesis, gene disruption using homologous recombination or/and insertion-deletion mutagenesis (Datsenko K. A. and Wanner B. L., Proc. Natl. Acad. Sci. USA, 2000, 97(12), 6640–6645).

The term "decreasing activity of the protein coded by ilvE gene" means that the protein coding sequence of ilvE gene or the expression regulation sequence of ilvE gene have been modified to have the enzymatic activity per cell decreased. Decreasing activity of the protein also can be performed by conventional methods, such as mutagenesis treatment using UV irradiation or nitrosoguanidine (N-methyl-N'-nitro-N-nitrosoguanidine) treatment, or site-directed mutagenesis followed by selection of the bacterium with desired phenotype. A bacterium having the "leaky-type" mutation in the said protein also can be used in the present invention. Protein having leaky type mutation is a mutant protein wherein the sequence change does not entirely abolish its activity (Lewin B., Genes VII, Oxford Press, 2000, p. 16)

Also, the bacterium of the present invention may be a bacterium belonging to the genus *Escherichia*, which produce L-valine, L-isoleucine and L-homoleucine in an amount of less than 1% of that of L-leucine produced, and activity of the protein coded by tyrB gene is increased.

The term "an activity of a protein coded by tyrB gene is increased" means that the molecule amount of the protein in a cell is increased, or that the activity per the protein itself is increased. The tyrB gene codes for aromatic amino acid transaminase (397 amino acid residues), which catalyzes, with using glutamate as the amino donor, a transamination of the α-ketoacids such as phenylpyruvate and 4-hydroxyphenylpyruvate into amino acids such as phenylalanine and tyrosine, respectively. But the term "activity" here means the activity to convert α-ketocaproate into L-leucine with glutamate as the amino doner (*Escherichia coli* and *Salmonella*, Second Edition, Editor in Chief: F. C. Neidhardt, ASM Press, Washington D.C., 1996). The tyrB gene (numbers 4264693 to 4265886 in the GenBank accession number NC_000913.1, gi:16131880) is located between alr and aphA genes.

Techniques for increasing the activity of the protein, especially techniques for increasing the molecule amount of the protein in a cell, include increasing the copy number of the gene and alteration of expression regulation sequence or enhancer sequence of a DNA coding for the protein of present invention, but are not limited thereto.

The term "transformation of a bacterium with a DNA containing tyrB gene" means introduction of the DNA into bacterium cell for example by conventional methods to increase copy number of gene. The copy number of the gene may be increased by insertion of a gene into a multicopy vector to form a recombinant DNA, followed by introduction of the recombinant DNA into microorganism. Vectors used for introduction of the recombinant DNA are exemplified by plasmid vectors such as pMW118, pBR322, pUC19, pET22b, pACYC184 or the like, phage vectors such as 11059, 1BF101, M13 mp9, Mu phage (Japanese Patent Application Laid-Open No. 2-109985) or the like and transposon (Berg, D. E. and Berg, C. M., Bio/Technol., 1, 417 (1983)), such as Mu, Tn10, Tn5 or the like. It is also possible to increase the copy number of a gene by integration the gene into a chromosome by a method utilizing a plasmid for homologous recombination or the like.

The technique of altering an expression regulation sequence or enhancer sequence can be combined with the technique based on the multiplication of gene copies.

For breeding a microorganism belonging to the genus *Escherichia* and having an increased expression amount of the gene, necessary regions of gene may be obtained by PCR (polymerase chain reaction) mainly based on already available information about *E. coli* genes. For example, tyrB gene can be cloned from the chromosome DNA of *E. coli* K12 or *E. coli* MG1655 strains using a PCR technique. The chromosome DNA used for this may be derived from any other strain of *E. coli*.

An alteration of expression regulation sequence of a DNA coding for tyrB protein can be achieved by locating the tyrB structural gene under control of a potent promoter. For example, lac promoter, trp promoter, trc promoter, $P_L$ promoter of lambda phage are known as potent promoters. Alternatively, a promoter can be enhanced by, for example, introducing a mutation into the promoter to increase a transcription level of a gene located downstream of the promoter. Further, it is known that substitution of several nucleotides in spacer between ribosome binding site (RBS) and start codon and especially the sequences immediately upstream of the start codon profoundly affect the mRNA translatability (Gold et al., Annu. Rev. Microbiol., 35, 365–403, 1981; Hui et al., EMBO J., 3, 623–629, 1984).

Furthermore, to increase the transcription level of the gene an enhancer may be newly introduced. Introduction of DNA containing either gene or promoter into chromosome DNA is described in, for example, International Patent Publication WO00/18935 and Japanese Patent Application Laid-Open No. 1-215280.

The bacterium of the present invention may be further improved by enhancing the expression of one or more genes involved in the L-leucine biosynthesis. Such genes are exemplified by a gene among L-leucine operon, i.e. leu operon, which preferably comprises a gene coding for isopropylmalate synthase (leuA gene, numbers 81958 to 83529 in the GenBank accession number NC_000913.1, gi:16128068) of which feedback inhibition by L-leucine is desensitized (European patent EP1067191). L-leucine operon also comprises leuB (gi:16128067), leuC (gi:16128066) and leuD (gi:16128065) genes (numbers 80867 to 81961; 79464 to 80864; and 78848 to 79453 in the GenBank accession number NC_000913.1, respectively).

As a parental strain, which is to be inactivated in activity of the branched chain amino acids transaminase encoded by ilvE gene and enhanced in activity of the aromatic amino acid transaminase encoded by tyrB gene, the bacteria belonging to the genus *Escherichia* such as *E. coli* strain K12, *E. coli* strain W1660 and the like may be used. Also it is possible to use as a parental strain the L-leucine producing bacteria belonging to the genus *Escherichia* such as *E. coli* strains H-9068 (ATCC 21530), H-9070 (FERM BP-4704) and H-9072 (FERM BP-4706) resistant to 4-azaleucine or 5,5,5-trifluoroleucine (U.S. Pat. No. 5,744,331), *E. coli* strains in which feedback inhibition of isopropylmalate synthase by L-leucine is desensitized (European patent EP1067191), *E. coli* strain AJ11478 resistant to β-2-thienylalanine and β-hydroxyleucine (U.S. Pat. No. 5,763,231) and the like.

Methods for preparation of plasmid DNA, digestion and ligation of DNA, transformation, selection of an oligonucleotide as a primer and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

2. Method of the Present Invention

The method of the present invention is a method for producing the L-leucine, which method comprises the steps of cultivating the bacterium of the present invention in a culture medium to produce and accumulate the L-leucine in the medium, and collecting the L-leucine from the medium.

In the present invention, the cultivation, the collection and purification of L-amino acid from the medium and the like may be performed in a manner similar to the conventional fermentation method wherein an amino acid is produced using a bacterium.

A medium used for culture may be either a synthetic medium or a natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate, and digested fermentative microorganism are used. As minerals, potassium monophosphate, magnesium sulfate, sodium chloride, ferrous sulfate, manganese sulfate, calcium chloride, and the like are used. As vitamins, thiamine, yeast extract and the like are used.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then L-leucine can be collected and purified by ion-exchange, concentration and crystallization methods.

EXAMPLES

Figure 1:
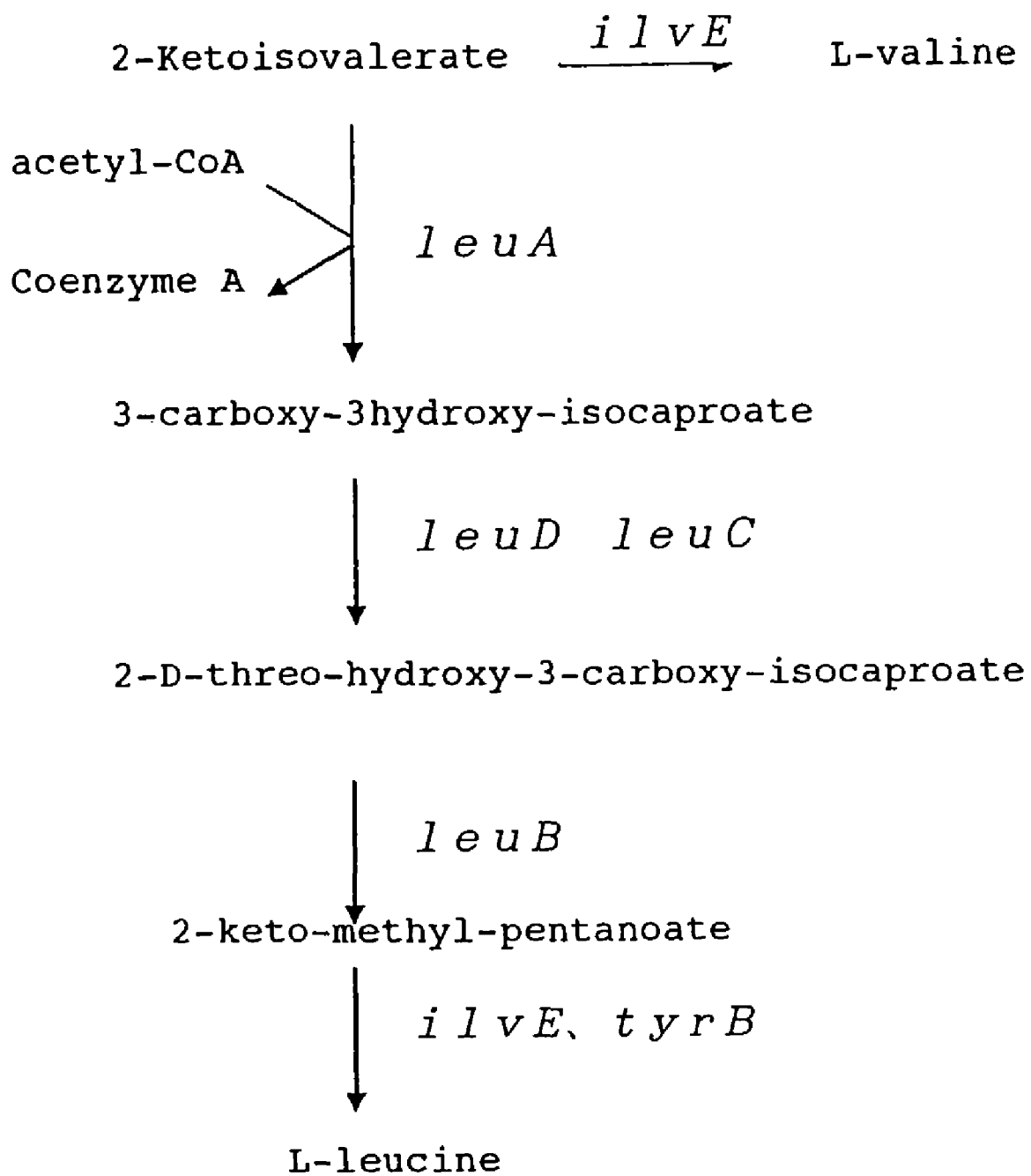
FIG. 1 shows L-leucine and L-valine metabolic pathways.

The present invention will be more concretely explained below with reference to Examples.

Example 1

Preparing the L-Leucine Producing Bacterium Belonging to the Genus *Escherichia*

The cells of wild type strain *E. coli* K12 (VKPM B-7) was treated with a mutagen, N-methyl-N'-nitro-N-nitrosoguanidine (0.05 mg/ml), for 20 min at 37° C., washed 4 times with physiological solution and plated on minimal agar medium M9 supplemented with 4.0 mg/ml DL-4-azaleucine. The plates were incubated for 5 days at 37° C. Colonies appeared on the plates were picked up and purified by streaking on the L-agar plates. The best of the obtained mutant resistant to DL-4-azaleucine, the mutant 55, produced 2.1 g/l of L-leucine and 0.8 g/l L-valine (Table 1, see below). This strain *E. coli* 55 has been selected and was used for induction of double L-isoleucine and L-valine auxotrophy. The numerous amounts of double auxotrophs, requiring L-isoleucine and L-valine for growth, were obtained. Among the obtained double auxotrophs, the best L-leucine producer, strain 505 producing 1.3 g/l of L-leucine, has been selected. The strain did not produce any amount of L-valine and L-isoleucine, but the double auxotrophs led to decrease of L-leucine production.

Double L-isoleucine and L-valine auxotrophy was caused by mutation in the ilvE gene. It was proved by the fact that introduction the plasmid containing ilvE gene (U.S. Pat. No. 5,120,654) into the strain 505 complemented double L-isoleucine and L-valine auxotrophy. Moreover, the measuring of enzymatic activity of the branched chain amino acid aminotransferase coded by ilvE gene in the strain 505 using 2-ketoisovalerate as substrate showed absence of its activity. Condition for measuring the enzymatic activity described by Coller R. H. and Kohlhaw G. (Nonidentity of the aspartate and the aromatic aminotransferase components of transaminase A in *E. coli*. J. Bacteriology, 1972, 112(1), p. 365–371).

The strain *E. coli* 505 has been deposited in the Russian National Collection of Industrial Microorganisms (VKPM)

(Russia 113545, Moscow, 1 Dorozhny proezd, 1) on May 14, 2001 under accession numbers VKPM B-8124.

Example 2

Cloning the tyrB Gene from *E. Coli* into pACYC184 Plasmid

The chromosomal fragment of *E. coli* K12 strain (VKPM-7), containing the tyrB gene was amplified by the PCR method, using two primers: primer 1 (SEQ ID NO:1) and primer 2 (SEQ ID NO:2) shown in the Sequence Listing. The primers 1 and 2 (24-mers) contain sequence including BamHI and HindIII sites, respectively, tagged at 5'-ends. Then, BamHI-HindIII fragment of 1.7 kb was ligated into corresponding sites of the plasmid pACYC184 (Chang, A. C. Y. and Cohen, S. N., Construction and characterization of amplifiable multicopy DNA cloning vehicles derived from the P15A cryptic miniplasmid, J. Bacteriol., 134, 1141–1156, 1978. Rose, R. E., The nucleotide sequence of pACYC184, Nucleic Acids Res., 16, 355, 1988), yielding the plasmid pACYC-tyrB. The plasmid pACYC-tyrB was introduced into cells of the strain *E. coli* 505 by transformation, and the strain 505/pACYC-tyrB was constructed.

g/l chalk (pH 7.2). Glucose and chalk were sterilized separately.

After cultivation the plasmid stability was determined by conventional method. The amount of L-leucine accumulated in the medium was determined by TLC. Liquid phase composition for TLC was as follows: isopropanol—80 ml, ethylacetate—80 ml, $NH_4OH$ (30%)—25 ml, $H_2O$-50 ml.

TABLE 1

| Strain | Amount of L-leucine, g/l | Amount of L-valine, g/l | Amount of L-isoleucine, g/l | Amount of L-homoleucine, g/l |
|---|---|---|---|---|
| 55 | 2.1 | 0.8 | 0.2 | 0.02 |
| 505 | 1.3 | <0.01 | <0.01 | <0.01 |
| 505/pACYC-tyrB | 2.7 | <0.01 | <0.01 | <0.01 |

As it is seen from Table 1, strains 505 and 505/pACYC-tyrB did not produce any amount of L-valine, L-isoleucine and L-homoleucine. The inactivation of the ilvE gene brought about the decrease in L-leucine production. And amplification of tyrB gene improved the L-leucine accumulation by the L-leucine producing strain 505.

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic DNA

<400> SEQUENCE: 1
agccgggatc cggtcatttt atgg                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic DNA

<400> SEQUENCE: 2
ttgggataag cttaacaata aaac                                          24
```

Example 3

Effect of the tyrB Gene Amplification on L-Leucine Production

Each of the strains 55, 505, 505/pACYC-tyrB was transferred by one loop of culture in 20-ml test tubes with L-broth and was incubated overnight with aeration at 32° C. The 0.1 ml of each night culture was transferred into the 20-ml test tubes (inner diameter 22 mm), suspended in 2 ml of medium for fermentation and cultivated at 32° C. for 48 hours with rotary shaker. The medium for fermentation contained 60 g/l glucose, 25 g/l ammonium sulfate, 2 g/l $KH_2PO_4$, 1 g/l $MgSO_4$, 0.1 mg/l thiamine, 5 g/l yeast extract Difco and 25

What is claimed is:

1. An isolated L-leucine producing bacterium belonging to the genus *Escherichia* which produces L-leucine, L-valine, L-isoleucine and L-homoleucine, wherein the amount of L-valine, L-isoleucine, and L-homoleucine produced is less than 1% of that of L-leucine produced, wherein the bacterium is *Escherichia coli* strain 505 which has been deposited in the Russian National Collection of Industrial Microorganisms under accession number VKPM B-8124.

2. An isolated L-leucine producing bacterium, wherein the bacterium is *Escherichia coli* strain 505 further modified to increase the activity of the protein coded by the tyrB gene of *Escherichia coli*, wherein said increase is obtained by increasing the copy number of said tyrB gene, or by locating said tyrB gene under control of a potent promoter.

3. A method for producing the L-leucine, which method comprises the steps of:

cultivating the bacterium according to claim 1 in a medium to produce and accumulate the L-leucine in the medium, and collecting the L-leucine from the medium.

4. A method for producing L-leucine, which method comprises the steps of:

cultivating the bacterium according to claim 2 in a medium to produce and accumulate the L-leucine in the medium, and collecting the L-leucine from the medium.

\* \* \* \* \*